United States Patent [19]

Columbus

[11] 4,169,060

[45] * Sep. 25, 1979

[54] BLOOD-COLLECTING AND SERUM-DISPENSING DEVICE

[75] Inventor: Richard L. Columbus, Rochester, N.Y.

[73] Assignee: Eastman Kodak Company, Rochester, N.Y.

[*] Notice: The portion of the term of this patent subsequent to Mar. 15, 1994, has been disclaimed.

[21] Appl. No.: 844,949

[22] Filed: Oct. 25, 1977

[51] Int. Cl.² .............................................. B01D 21/26
[52] U.S. Cl. ........................ 210/516; 210/DIG. 23; 233/26
[58] Field of Search .................. 210/83, 84, 514–518, 210/DIG. 23, DIG. 24; 222/1, 23, 52, 401, 420, 207; 233/1 A, 1 R, 26; 23/203 B, 259; 73/61.1 C, 425.4 P, 425.4 R, 425.2; 128/2 F, 218 M, 220, 272; 141/275; 206/216, 525

[56] References Cited

U.S. PATENT DOCUMENTS

| 3,508,653 | 4/1970 | Coleman | 210/83 |
|---|---|---|---|
| 3,779,383 | 12/1973 | Ayres | 210/84 |
| 3,852,194 | 12/1974 | Zine | 210/83 |
| 3,887,466 | 6/1975 | Ayres | 210/131 |
| 3,891,553 | 6/1975 | Ayres | 210/136 |
| 3,894,951 | 7/1975 | Ayres | 210/136 |
| 3,894,952 | 7/1975 | Ayres | 210/136 |
| 3,897,340 | 7/1975 | Ayres | 210/314 |
| 3,897,343 | 7/1975 | Ayres | 210/516 |
| 3,909,419 | 9/1975 | Ayres | 210/518 |
| 3,929,646 | 12/1975 | Adler | 210/359 |
| 3,977,568 | 8/1976 | Smith | 222/80 |
| 4,012,325 | 3/1977 | Columbus | 210/516 |
| 4,052,320 | 10/1977 | Jabubowicz | 210/DIG. 23 |
| 4,055,501 | 10/1977 | Cornell | 210/516 |

Primary Examiner—Frank Sever
Attorney, Agent, or Firm—Dana M. Schmidt

[57] ABSTRACT

A device is provided for collecting and separating a two-phase liquid, and for dispensing the light phase. The device provides improved structure such that the dispensing aperture is protected from premature liquid contact by a partition. Upon phase separation, the partition automatically allows flow of the light phase to the aperture.

8 Claims, 10 Drawing Figures

BLOOD-COLLECTING AND SERUM-DISPENSING DEVICE

BACKGROUND OF THE INVENTION (1) Field of the Invention

This invention relates to a device for the collection, phase separation, and serum dispensing, of two-phase liquids such as blood.

(2) State of the Prior Art

Blood collection and phase separation devices have long recognized the necessity for a partition which will maintain phase separation of serum and cells after separation is achieved by centrifugation. Movable mechanical "pistons" were first used for this purpose. Subsequent movable partitions incorporated filters so that the clogging of the filters with fibers and cells of the heavier phase would automatically terminate movement of the pistons at the fluid interface.

To avoid the oft-times elaborate piston constructions of the type noted above, certain researchers turned to the use of thixotropic, inorganic gels for the partition, either alone or in combination with mechanical piston-like members, as disclosed for example in U.S. Pat. No. 3,909,419 issued on Sept. 30, 1975. Because of the specific gravity of the gel and/or the incorporated mechanical pieces, the phase separation interface was automatically reached by the partition.

However, none of the preceding approaches contemplate the incorporation of a dispensing chamber with the collecting and phase separating device.

U.S. Pat. No. 3,977,568 issued Aug. 31, 1976 discloses devices having a dispensing chamber coupled with a blood collection compartment to permit closed flow from one to the other. These devices obviate exposure of the serum to the atmosphere and the operator. The disclosed arrangements require the use of at least one valve disposed between the separating compartment and dispensing chamber, to protect the serum-collecting end of the phase separation compartment from whole blood contamination, and at least one step by an operator is required to actuate the valve.

SUMMARY OF THE INVENTION

It is an object of this invention to provide a blood collecting and serum dispensing device which protects the dispensing portion from whole blood but also automatically opens up the dispensing portion of the device to serum flow, by the phase-separation step.

It is a related object of this invention to provide a blood collecting device which automatically converts into a serum drop dispensing device during phase separation, without any separate intervention by an operator.

Other objects and advantages will become apparent upon reference to the following Summary and Description, when read in light of the attached drawings.

These objects are accomplished by a blood collection and serum dispensing device wherein the partition used to separate the two blood phases is also used to protect the dispensing aperture from whole blood contamination, and to automatically allow flow of serum to the aperture upon phase separation. More specifically, there is provided a blood-collecting, phase-separating and serum-dispensing device comprising an elongated container having a blood collection and phase separation compartment and a dispensing chamber, the compartment including means defining a blood inlet and the chamber having means defining a drop-dispensing platform and a dispensing aperture, and a partition having a specific gravity between that of blood cells and blood serum, the partition being disposed in the container at a first position wherein it blocks flow of whole blood within the compartment from the inlet to the aperture and being movable, in response to a phase-separating centrifugal force directed from the chamber towards the compartment, to a second position within the container between separated blood serum and separated blood cells, whereby separated serum can flow to the chamber aperture.

DESCRIPTION OF THE PREFERRED EMBODIMENT

Figure 1:
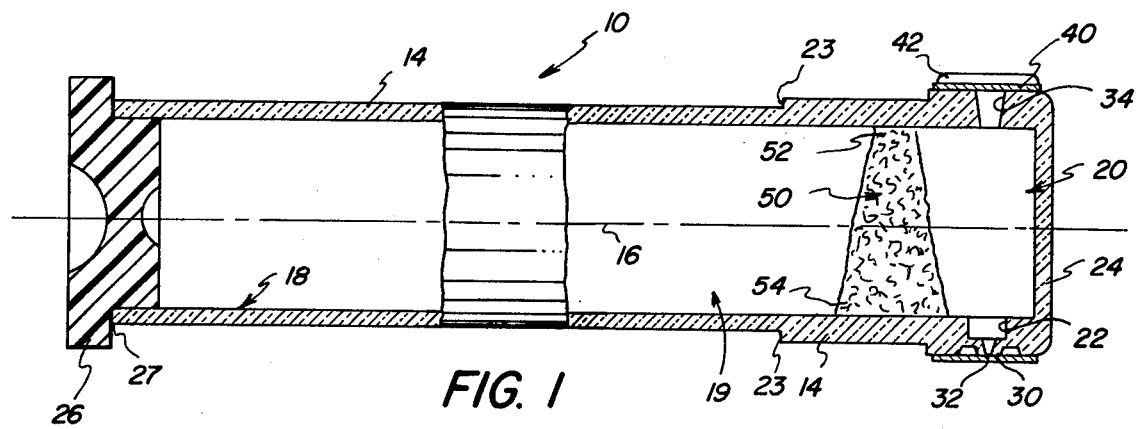
FIG. 1 is a longitudinal view partly in section of a device constructed in accordance with the invention.

The device illustrated in FIG. 1 comprises an elongated container or tube 10 having opposed walls 14 arranged about an axis 16 to define a blood collection and phase separation compartment 18 at one end of container 10 and a dispensing chamber 20 at the other end. One portion 19 of compartment 18 is the serum-collecting portion during phase separation, hereinafter described. Chamber 20 can be considered the entire other end, and includes a recessed portion 22 in wall 14. The walls 14 can be cylindrical for the length of tube 10 or compartment 18 can be cylindrical with chamber 20 being squared, as shown, commencing at ridges 23. End wall 24 completes chamber 20. To provide a blood inlet, a removable elastomeric septum 26 is positioned at the open end 27 of compartment 18. Septum 26 is penetratable by a syringe needle or cannula 28 in a conventional manner, FIG. 2A, to allow access to the device by whole blood B.

Recessed portion 22 is provided with a drop-dispensing platform 30 which in turn has an aperture 32. Platform 30 and aperture 32 are formed to permit only pressurized flow of serum therethrough, and not flow under the influence of gravity alone. Preferably, platform 30 and aperture 32 include the features disclosed in *Research Disclosure*, Vol. 133, May 1975, Publication No. 13360, published by Industrial Opportunities Limited, Homewell, Havant Hampshire P091EF, United Kingdom, the details of which are expressly incorporated herein by reference. Such features permit the formation of a predictable-volume pendant drop no matter what peculiar viscosity and surface tension might exist in a given patient's blood serum.

Aperture 34 allows pressurization of the chamber, as hereinafter described.

In accordance with one aspect of the invention, a partition 50 is incorporated in container 10 at a first position where it temporarily prevents or blocks flow of liquid, e.g., of whole blood, to aperture 32 as it is collected at end 27. As shown in FIG. 1, this position is one in which it is adjacent portion 19 of the compartment and preferably within chamber 20. The partition contacts walls 14 around their entire circumference, but is spaced away from wall 24 a sufficient distance as to not cover aperture 32. The partition is the sole blocking means protecting aperture 32, because no movable operator-controlled valve is included. In this embodiment, the partition comprises an inorganic thixotropic polymeric gel inert to blood serum. Although the composition of such gel is not critical, so long as the aforesaid properties exist, convenient and preferred compositions include those described in *Research Disclosure*, Vol. 152, December 1976, Publication No. 15247, the details of which are expressly incorporated herein by reference. Preferably, for reasons hereinafter described, the gel partition is thinner at top portion 52 than at the bottom portion 54.

The gel can be inserted as shown, spaced from wall 24, by a dispenser which ejects the gel into container 10 at this position.

Optional features of container 10 include a removable cover disposed over the exterior surface of platform 30. If used, preferably it is wrapped around chamber 20 as a strip 40 so as to overlay both apertures 32 and 34. Strip 40 has a convenient pull tab 42 at one end. Such a strip prevents the apertures from being contaminated by dirt and the like and insures that the pendant drop capability of platform 30 is not upset by contact with surfactants or oils such as exist on human skin. By constructing strip 40 from a metallic foil, it can be vacuum-sealed around the entire circumference of container 10 at chamber 20, thereby sealing apertures 32 and 34 and allowing the device to be air-evacuated, a common embodiment for ease in drawing whole blood. Or alternatively, strip 40 can comprise a perforated material to permit the device to be atmosphere-vented, whereby only the patient's blood pressure is used as the filling force. Or still further, a microporous filler (not shown) can be included in compartment 18 to assist in collecting the blood in the vented mode, in the manner shown in *Research Disclosure*, Vol. 159, July 1977, Publication No. 15918, published as noted above.

Figure 2A:
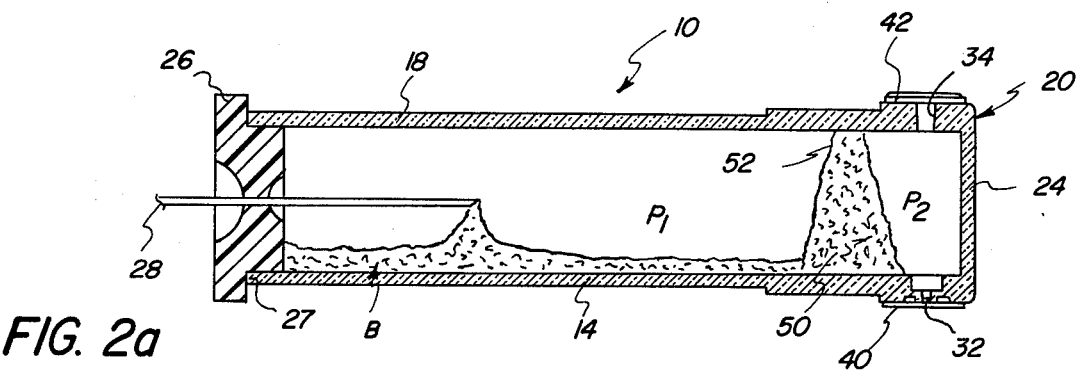
FIGS. 2A through 2D are sectional views similar to that of FIG. 1, illustrating a preferred use of the device.
Figure 2B:
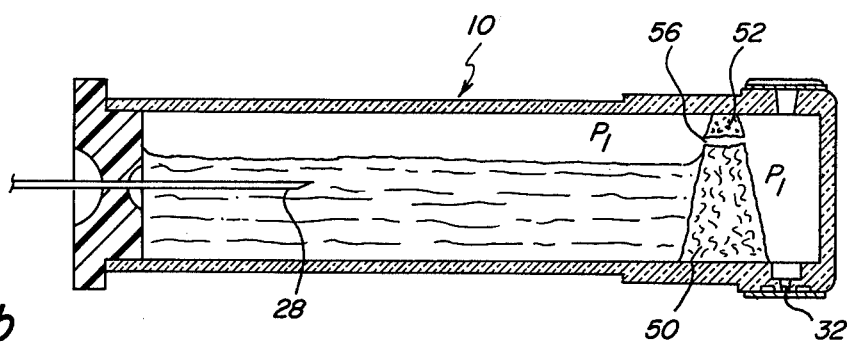

The first step in the use of the device, FIG. 2A, is to insert needle 28 through the septum 26, whereby either the vacuum assists in pulling in whole blood B, or the patient's pressure fills the device if vented as described above. Partition 50 prevents the whole blood from contaminating aperture 32. No matter which of these collection modes is used, eventually the pressure will build up to a level $P_1$, which exceeds the pressure $P_2$ in the chamber 20, and punch-through 56, FIG. 2B, will occur in the gel of partition 50, equalizing the pressures. By coating the gel so that it is thinner at its upper portion 52, the punch-through forms at the upper portion and does not jeopardize the protection of aperture 32.

Alternatively, the gel can have uniform thickness if its thixotropic flow characteristics are such as to automatically seal over any punch-through which occurs during pressure equilibration.

Figure 2C:
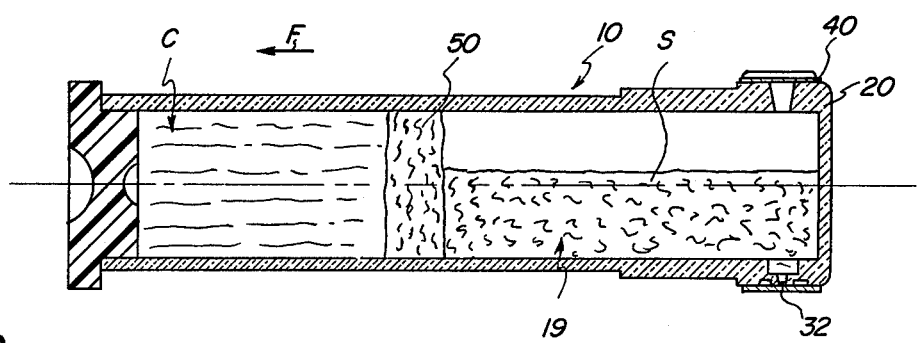
Figure 2D:
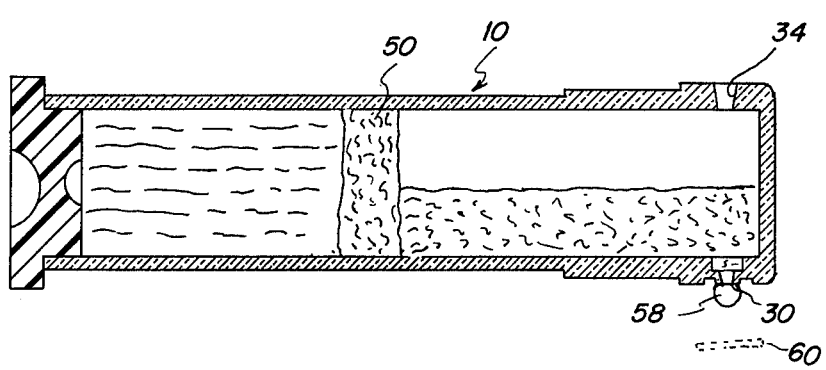

Phase separation is achieved by centrifugation, which utilizes a centrifugal force F directed from chamber 20 to compartment 18, FIG. 2C. During centrifugation, and in automatic response to the force F, partition 50 reforms at the phase separation boundary while blood serum, the lighter phase, flows through the gel. When reformed, partition 50 provides a barrier to maintain separation between the blood cells C and the serum S. At the same time, the partition is now in a position, without any need for operator intervention, where it no longer blocks aperture 32 from the flow of serum thereto, obtained from the whole blood during the phase separation. That is, the gel when reformed no longer is between aperture 32 and separated blood serum, so that serum flows freely to the aperture. Removal of strip 40, if used, uncovers platform 30, FIG. 2D, and aperture 34 can be used to pressurize the device (against partition 50 acting as a plug), as described in the aforesaid U.S. Pat. No. 4,012,325, to form a pendant drop 58 to be touched off to a substrate 60 for analysis.

The container 10 is preferably formed from a moldable plastic, such as copolymers acrylonitrile-butadiene-styrene, or polymers such as polypropylene, polystyrene, polyethylene, etc.

Although the preferred location of platform 30 is as shown, it can also be located in end wall 24, in which case container 10 would be oriented vertically for drop dispensing, instead of horizontally as in FIG. 2.

It is possible to draw the serum out through aperture 32 by the use of a negative pressure differential, that is, by using a pressure at the exterior of platform 30 which is less than the pressure inside chamber 20 (e.g., a partial vacuum). In such a case, aperture 34 can be eliminated and aperture 32 can be used after drop touch-off to equilibrate the system. That is, after touch-off, air bubbles into chamber 20 through aperture 32 to replace the volume of the dispensed drop.

Figure 3:
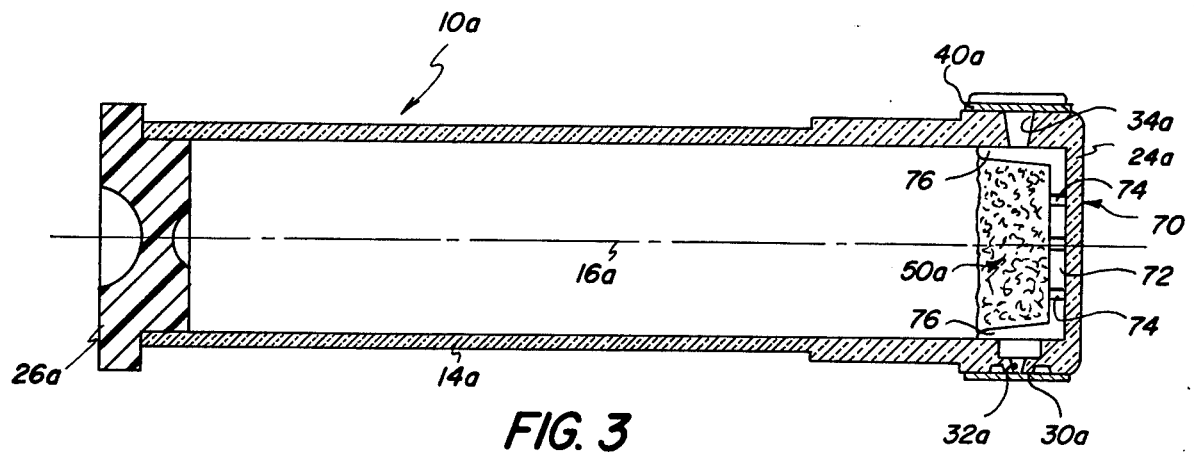
FIG. 3 is a sectional view similar to that of FIG. 1, but of an alternate embodiment.
Figure 4:
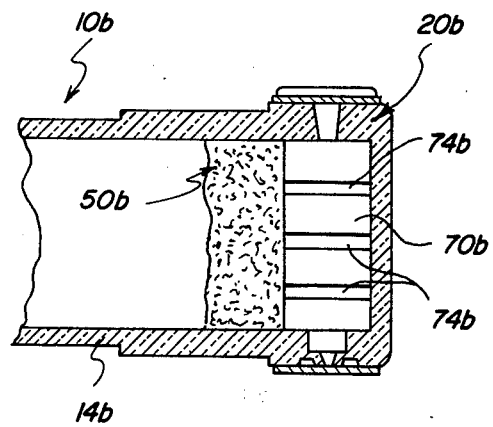
FIG. 4 is a fragmentary sectional view, similar to that of FIG. 3, of yet another embodiment.

The partition can be gel, as described above, or it can comprise a combination of gel and a so-called rigid member, FIGS. 3 and 4, the currently preferred embodiments. Parts similar to those previously described have the same reference numberal, to which the distinguishing suffixes "a" and "b" have been added. "Rigid" is used here to distinguish from materials having variable shapes and forms, such as that of gel. Preferably it also remains at the cell-serum interface after phase separation, and thus has a specific gravity between that of blood cells and blood serum; e.g., about 1.06. Materials suitable for such rigid members include polystyrene.

Thus, FIG. 3, container 10a comprises a tube having walls 14a shaped as before, with septum 26a and end wall 24a closing the ends of the tube. Platform 30a, apertures 32a and 34a, and optional strip 40a function as in the previously-described embodiment. The partition, however, comprises the gel 50a of the previous embodiment together with a perforated member or plate 70 initially in contact with wall 24a and comprising a base 72 having a plurality of spaced apertures of orifices 74 oriented generally parallel to tube axis 16a, and an annular flange 76. Flange 76 extends far enough away from base 72 to cover apertures 32a and 34a. To properly initially bias the plate within chamber 20, flange 76 is preferably formed so that, when plate 70 is free-standing, the flange projects outwardly beyond the maximum width of base 72 a distance sufficient to cause a biasing seal of the flange to chamber 20a, when inserted therein, to prevent any blood leakage to aperture 32, but insufficient to prevent the plate from moving, when centrifuged, with gel 50a.

Gel 50a can be disposed entirely within flange 76, extending into orifices 74, or it can extend into contact with walls 14a.

As will be apparent, orifices 74 serve to allow serum to pass through plate 70 while it moves with the gel during centrifugation to the forming phase interface. In this manner, the combined gel-plate partition unblocks flow of serum to aperture 32a.

Alternatively, FIG. 4, the device of the invention can comprise container 10b wherein the compartment, chamber and gel are as described before, but there is included a rigid disc 70b of specific gravity of about 1.06, the disc having a plurality of apertures or orifices 74b formed as in the previously-described embodiment. No flanges are provided, however, and a force-fit of disc 70b in chamber 20b is unnecessary due to the sealing contact of gel 50b with walls 14b.

Therefore, the partition temporarily blocking liquid access to the dispensing aperture, capable of automatic movement during centrifuging to unblock the access, can be either just a gel or it can be a gel-rigid member combination. The gel-rigid member combination has the advantage of requiring less gel.

Such a combination of rigid member and gel functions as a single unit that performs the blocking and unblocking functions attributed in the previous embodiment to the gel alone. As used in this context in the specification and claims, the term single "unit" thus includes such a combination, the gel alone, or as described hereinafter, a mechanical equivalent of the gel alone.

It is further contemplated that a rigid member can be used in place of the gel as the movable partition which protects the dispensing aperture from whole blood. For example, the pistons disclosed in U.S. Pat. Nos. 3,891,553; 3,894,951; 3,894,952; and 3,897,340, utilizing filters to insure automatic relocation of the pistons at the phase separation interface, can be used.

Figure 5:
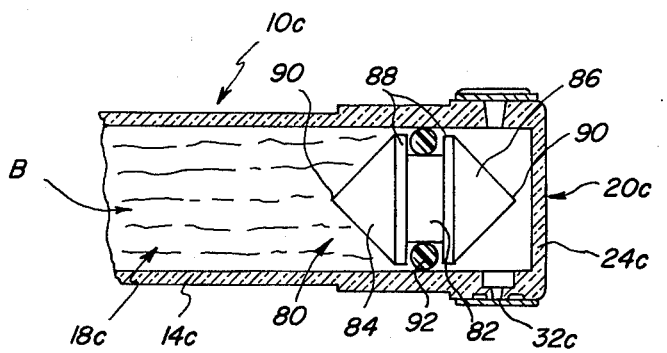
FIGS. 5 through 7 are fragmentary sectional views similar to that of FIG. 4, illustrating the use of still another embodiment.
Figure 6:
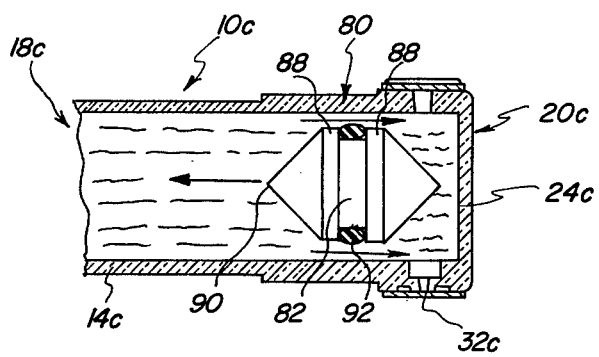
Figure 7:
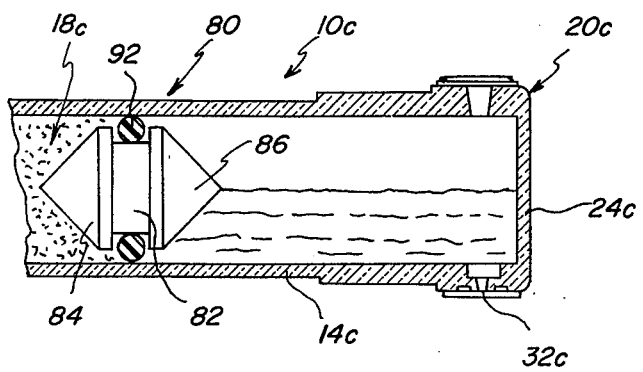

Alternatively, a piston with a collapsible o-ring seal, FIGS. 5–7, can be used. Parts similar to those previously described bear the same reference numeral to which the distinguishing suffix "c" has been applied. Thus, container 10c is constructed as described above, walls 14c defining blood collection and phase separation compartment 18c and dispensing chamber 20c. The gel however has been entirely replaced by a piston 80, disposed a sufficient distance away from end wall 24c as to be inbetween compartment 18c and dispensing aperture 32c. Piston 80 is constructed similarly to that shown in U.S. Pat. No. 3,897,343, issued July 29, 1975, although its location in the device is different. Specifically, piston 80 comprises a body portion 82 of a general cylindrical shape, which terminates at opposite ends in cones 84 and 86 of essentially identical construction. Each cone has a shoulder 88 and a point 90, the outer diameter of shoulders 88 being sufficiently greater than that of body portion 82 (and less than the inner diameter of walls 14c) as to longitudinally confine between the shoulders an elastomeric, compressible, annularly-shaped material 92. A preferred construction of material 92 is an o-ring of a closed-cell polymeric material, such as rubber, having a free outer diameter (e.g., at zero hydrostatic pressure) which seals it both against walls 14c and against body portion 82, preventing flow of whole blood B, FIG. 5, to aperture 32c. However, under hydrostatic forces of the type generated in blood during centrifuging, ring 92 collapses, FIG. 6, and for this reason the axial spacing between shoulders 88 is greater than the non-compressed cross-section diameter of ring 92, FIG. 5, by an amount sufficient to accommodate the collapsed shape of the ring, FIG. 6.

The total specific gravity of the piston 80 is, of course, between that of the blood cells and serum, or approximately 1.06. Polystyrene can be used, as noted above. Points 90 of the cones are utilized solely to facilitate flow of the piston relative to serum during centrifuging, and the primary reason for using two cones 84 and 86 is to make the piston non-end-specific. It can be inserted into the device either way.

The use, then, of container 10c is as follows: As centrifugation starts, FIG. 6, hydrostatic pressures build up and collapse o-ring 92, to allow the light phase, serum, to flow relative to the piston. The piston then seeks out the serum-cell interface with the o-ring so collapsed. After centrifugation ceases, the o-ring returns to a sealing configuration with walls 14c, FIG. 7, leaving the serum free access to dispensing aperture 32c.

Ring 92 of piston 80 will also allow equalization of air pressures in the container during the blood collection phase. Until such equalization occurs, it may be desirable to orient container 10c so that chamber 20c is oriented above the septum. Thereafter, container 10c can be handled without concern about blood flow to aperture 32c, as o-ring 92 will maintain the necessary seal against such flow.

Additional embodiments which can utilize the disclosed invention are those illustrated in *Research Disclosure*, Vol. 159, July 1977, Publication No. 15918, the details of which are expressly incorporated herein by reference. Specifically, the devices therein illustrated use a sliding dispensing head which acts as a valve. The head is slid into a closed position during blood collection, to prevent whole blood from reaching the dispensing aperture, and after phase separation is slid into an open position by an operator. However, by using this invention, such head is permanently fixed in an "open" position, and only the partition comprising the gel phase separator is used as described above to provide the blocking means preventing premature flow to the dispensing aperture.

The invention has been described in detail with particular reference to certain preferred embodiments thereof, but it will be understood that variations and modifications can be effected within the spirit and scope of the invention.

What is claimed is:

1. A blood-collecting, phase separating and serum-dispensing device comprising
    an elongated container having a blood collection and phase separation compartment and a dispensing chamber, said compartment including means defining a blood inlet, said chamber having means defining a drop-dispensing aperture sized to prevent gravity flow of blood serum therethrough, and means to permit flow of serum in response to differential pressures,
    and means positioned within said device for blocking flow of whole blood from said inlet to said dispensing aperture prior to phase separation of the blood, said means consisting of a single unit having a specific gravity between that of blood cells and blood serum, said unit being automatically movable in its entirety, in response to a phase-separating centrifugal force directed from said chamber towards said compartment, to a second position within said container between separated blood serum and separated blood cells,
    whereby only separated serum can flow to said chamber aperture.

2. A device as defined in claim 1, wherein said unit includes an inorganic thixotropic polymeric gel.

3. A device as defined in claim 1, wherein said unit includes a movable perforated plate covering said aperture and having a specific gravity between that of blood serum and blood cells.

4. A device as defined in claim 2, wherein said unit is disposed adjacent the serum collecting portion of said compartment and comprises a piston.

5. A device as defined in claim 4, wherein said piston comprises
a body portion which is generally cylindrical and has a diameter less than the internal diameter of the blood collection compartment; and
an elastomeric material mounted on said body portion so as to form a seal between said piston and said compartment, said material being compressible in response to hydrostatic forces so that serum can flow therepast.

6. A device as defined in claim 1, and further including a protective cover over the exterior surface of at least said dispensing aperture of said dispensing chamber.

7. A blood-collecting and serum-dispensing device comprising
wall means arranged about an axis to define a blood collection and phase separation compartment having two opposed ends;
means defining a blood inlet adjacent one end of said compartment;
means defining a dispensing chamber adjacent the other end, said chamber including means defining a dispensing aperture, said aperture being sized to prevent gravity flow of blood serum therethrough, and means to permit flow of serum in response to differential pressure;
and means positioned in said device for blocking flow of whole blood within said compartment from said inlet to said dispensing aperture, said blocking means consisting of a single unit having a specific gravity between that of blood cells and blood serum and including at least an inorganic thixotropic polymeric gel inert to blood serum;
said unit being automatically movable in its entirety by the application of a phase-separating centrifugal force directed from said chamber towards said compartment, to a position between the separated phases of whole blood, whereby separated blood serum can flow to said aperture.

8. A device as defined in claim 7, wherein said blocking means include a movable perforated plate disposed so as to cover said aperture, said plate having a specific gravity between that of blood serum and blood cells so that it moves automatically upon centrifugation to a position permitting access to said aperture by blood serum while maintaining phase separation with said gel between the serum and the cells.

* * * * *

UNITED STATES PATENT AND TRADEMARK OFFICE
CERTIFICATE OF CORRECTION

PATENT NO. : 4,169,060

DATED : September 25, 1979

INVENTOR(S) : Richard L. Columbus

It is certified that error appears in the above-identified patent and that said Letters Patent are hereby corrected as shown below:

Column 7, line 3, "2" should read --1--.

Signed and Sealed this

Twentieth Day of May 1980

[SEAL]

Attest:

SIDNEY A. DIAMOND

Attesting Officer

Commissioner of Patents and Trademarks